United States Patent [19]

Rambert et al.

[11] 4,323,059
[45] Apr. 6, 1982

[54] ARTICULATED SPLINT FOR A KNEE JOINT

[76] Inventors: André Rambert, Les Fontanelles, 10, bis rue Docteur Bonhomme, Lyon 3e; Gilles Bousquet, Chemin de Marandon, Saint Etienne; François Rigal, Hopital Interdepartemental, Hauteville, all of France

[21] Appl. No.: 140,704

[22] Filed: Apr. 16, 1980

[30] Foreign Application Priority Data

Apr. 19, 1979 [FR] France ................................. 79 10960
Dec. 26, 1979 [FR] France ................................. 79 32140

[51] Int. Cl.³ ............................................... A61F 3/00
[52] U.S. Cl. ..................................... 128/80 C; 128/88
[58] Field of Search ................. 128/80 R, 80 C, 80 F, 128/83, 87 R, 88; 3/22

[56] References Cited

U.S. PATENT DOCUMENTS

| 1,390,915 | 9/1921 | Loth | 128/80 F |
| 2,460,895 | 2/1949 | Meany | 128/80 C |
| 3,902,482 | 9/1975 | Taylor | 3/22 |
| 4,111,195 | 9/1978 | Neufeld | 128/83 |

Primary Examiner—John D. Yasko
Attorney, Agent, or Firm—Browdy and Neimark

[57] ABSTRACT

An articulated splint for knee joint, of the type having two symmetrical portions each of which is made up of two uprights, an upper femoral one and a lower tibial one, are connected to one another by a rod. These uprights are to be fastened with their opposite number of the other portion, against one of the side faces of the corresponding part of a leg of a patient by a single cast covering the two portions of the splint and whose central part covering the knee is then cut out or eliminated. A first pin connects one of the uprights to the rod, this pin extending through the rod via an aperture whose longitudinal axis is oriented in the direction of a second connecting pin of the other upright on the rod. Pin-like members may be provided on the rod to limit the angular extent of possible movement of one or both of the uprights in one or both directions. The pin like members are threaded into respective threaded bores in the rod. Additional threaded bores may be provided to allow adjustment of the maximum angle of movement. A wing may be provided on the rod for assuring relative closing angular movement of one upright with respect to the other in a given direction.

11 Claims, 7 Drawing Figures

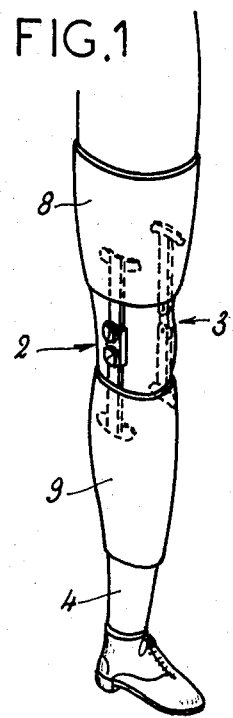
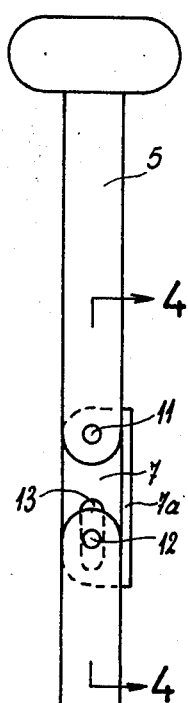
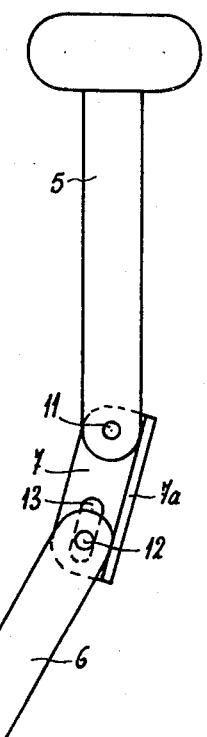
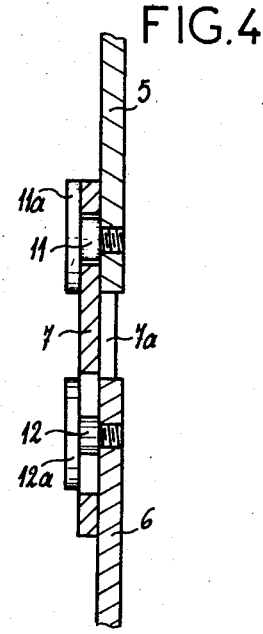

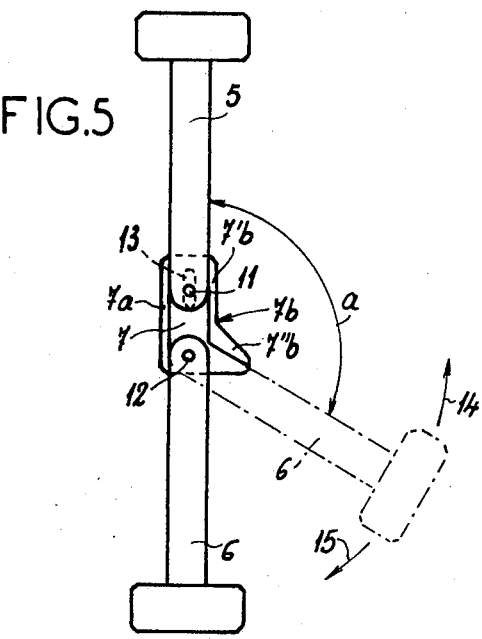
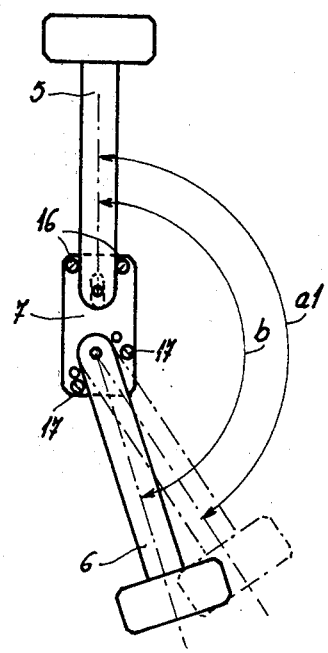
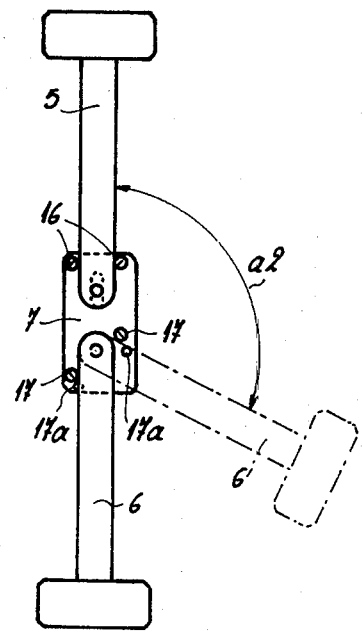

ARTICULATED SPLINT FOR A KNEE JOINT

BACKGROUND OF THE INVENTION

This invention relates to an articulated splint for the knee joint, i.e., a splint intended to function in conjunction with a cast or an orthotic sleeve constructed from other material such as plastic, felt, elastic and the like without blocking the knee joint. Such splints are used for treating fractures, re-education therapy of an arthrolysis, orthopedic treatment of limbs after surgical correction, early re-education therapy of ligamentous lesions and to provide restraining articulated orthoses for traumatic knee lesions and other knee injuries of the type which occur to athletes.

This type of splint generally is composed of two symmetrical side portions each of which is made up of two uprights, an upper femoral upright and a lower tibial upright, connected to one another by a rod. Each of the uprights is intended to be fastened, with its counterpart of the other side portion, against one of the lateral faces of the corresponding part of a leg by a single cast or the like covering both side portions of the splint whose central part covering the knee is then cut or eliminated.

Two general types of splints are now distinguished, these simply being monoaxial splints and polycentric splints.

Since the knee joint is a complex joint whose axis of rotation moves over a curve as a function of a well determined law, neither of the two types of splints mentioned above are satisfactory. By the very fact that the first is a simple articulation, its tibial element can only constitute a hindrance to the movements of the tibia, the axes of rotation of the splint and knee being able to coincide, at best, only in a particular determined angular position of the tibial in relation to the femur.

Of the polycentric splints, there are those each of whose uprights is coupled to the other by a rod and train of three gears of which two are keyed on connecting pins of the rod to each of the uprights and whose third gear, mounted free in rotation on a pin carried by the rod, meshes with each of the other two and connects them in rotation. In this splint, the connecting pin of the lower or tibial upright, consequently moves over an arc of a circle, which, although representing an advance in comparison with the monoaxial type splint, does not faithful reproduce the motion of the knee joint and as a result produces mechanical constraints contrary to the normal physiology of the knee.

There is further known a polycentric splint without a connecting pin and in which the two uprights of each its two side portions are connected to one another by a central part of high-density polyethylene, this type of splint functions by virture of deformation and is either too rigid, constituting an impediment, or too flexible, to accomplish its aim.

SUMMARY OF THE INVENTION

It is an object of the present invention to provide an articulated splint for a knee joint which overcomes the abovenoted shortcomings and drawbacks of the known polycentric and monoaxial splints.

For this purpose, in the splint to which the present invention, which is of the type wherein each of its portions is made up of two uprights joined to one another by a rod, the pin for connecting one of the uprights to the rod goes through an elongated aperture in that particular upright. The elongated aperture has its longitudinal axis oriented in the direction of the pin connecting the other upright on the rod.

Thus, the distances between the pins connecting the uprights to the rod and thus their respective axes are variable without being subjected to a determined law which allows the tibial uprights to accompany the tibia without ever hindering its movement despite the complexity of the knee joints.

The elongated aperture corresponds to the connecting pin of the tibial or femoral upright of the rod.

According to another characteristic of the present invention, to limit the rotation of the tibial upright to a single direction from its position of alignment with the femoral upright, the rod of each side portion exhibits, along its edge opposite that of the direction of the rotation of the tibial upright, a wing forming a stop for each of the two uprights.

According to still another characteristic of the present invention, to improve the crosswise holding of each side portion of this splint, the pin connecting each upright to the rod is made up of a pivot fixed to the corresponding upright and whose free end exhibits a shoulder, thus assuring the holding and guiding of the rod, the length of the pivot corresponding to the thickness of the rod increased by the play necessary for functioning.

In a general way, the splint is entirely satisfactory. However, in some cases, during the first re-education period, it is necessary to limit the angle of antero-posterior rotation. This limitation can be imposed, for example, after an operation on the cruciate ligaments by the knee, which is not possibly using the splint according to the basic embodiment of the described above.

For this reason, according to an improved variant embodiment of the invention, the rod of each side portion to which are connected the two uprights of the corresponding side portions carries means which limit the rotation of the two uprights, in one direction to their maximal opening position and in the other direction, to the desired lower maximum angle of bending.

According to a first embodiment of the variant, in the case where maximal opening position of the uprights in their position of alignment with one another, the means limiting in one direction the rotation of the two uprights of each element to that position and, in the other direction, to the desired maximum lower angular position, comprise, on the one hand, a first longitudinal wing integral with a straight edge of the rod and on the other hand, a second wing in the shape of a right-angle iron integral with the opposite edge of the rod, this edge, like the second wing, forming an angle at the desired lower maximum value of angulation of the two uprights.

According to a second embodiment of the variant the means limiting the rotation of the two uprights, in one direction to their maximal opening position and, on the other hand, to the desired lower maximum angle of bending, are made up of pins fastened to the rod, by any suitable technique, on the same side as the femoral and tibial uprights.

Preferably, each pin is fastened by screwing it in a threaded hole provided in the rod to receive the pin.

According to an advantageous third embodiment of this variant, the rod includes at least an additional threaded hole corresponding to another value of at least one of the desired maximum angles.

This arrangement makes possible not only the choice of the maximum angle, as a function of the patient to be treated, but also by modifying this angle and, particularly, increasing it, during re-education, as the patient continues to recover.

According to a preferred embodiment of the invention, the means limiting the rotation of the two uprights, in one direction to the maximal opening position and in the other direction, to the desired lower maximum angle of bending, are arranged so as to immobilize one of the uprights in rotation, preferably the upper femoral upright.

In this case, advantageously, the connecting pin which goes through the rod via an aperture is that on which the upper femoral upright is connected.

BRIEF DESCRIPTION OF THE DRAWING

In any case, the invention, is to be better understood from the following diagrammatic drawing figures representing by way of non-limiting example, embodiments of the articulated splint of the present invention.

FIG. 1 is a perspective view of a human leg which is provided with an articulated splint according to a first embodiment of the invention.

FIGS. 2 and 3 are respective side, elevation views respectively showing one side portion of the articulated splint of FIG. 1 in a straight position and a bent position.

FIG. 4 is a sectional view of the splint of FIG. 2, the section having been taken along section line 4—4.

FIG. 5 is a side elevation view, similar to that of FIG. 2, showing one, side portion of an articulated splint according to a second embodiment of the present invention.

FIGS. 6 and 7 are respective views similar to those of FIGS. 2 and 5 showing one side portion of an articulated splint according to a third embodiment of the present invention.

DETAILED DESCRIPTION OF THE PREFERRED EMBODIMENTS

As shown in FIG. 1, a splint is of the type made up of two symmetrical side portions, inside portion 2 and outside portion 3, respectively, intended to be fastened respectively to the inside and outside faces of a leg 4 of a patient.

Each portion 2,3 is made up of two uprights, an upper or femoral upright 5 and a lower or tibial upright 6 connected to one another by a central articulated rod 7.

The two portions 2, 3 of the splint are fastened to the leg 4 by a cast or the like which, originally may have entirely covered them and a considerable portion of the leg 4 including the knee. As shown the central part of the cast, which originally covered the knee of the patient, has been cut or removed to leave only two sleeves 8 and 9 which respectively surround the upper and lower uprights of the orthotic device and assure their being held against the femoral and tibial parts of the leg 4.

As shown particularly in FIGS. 2 and 3, the upper upright 5 is connected to the rod 7 by a pin 11, while the lower upright 6 is connected to it by a pin 12, the pins 11 and 12 being fastened respectively rigidly respectively to the uprights 5 and 6. The pin 12, serving to connect the lower upright 6 to the rod 7, goes through this latter via a longitudinal aperture 13, i.e., an aperture whose longitudinal axis is oriented in the direction of the pin 11 of the upright 5 for connecting it to the rod 7. Because of this arrangement, the distance between the pins 11 and 12 is variable so that during pivoting movement of the lower upright 6, the pin 12 is transversally mobile in relation to connecting pin 11.

The connecting pin 12 can consequently move freely in the aperture 13 during bending of the knee without imposing its own law of movement.

The splint of the present invention therefore, allows the patient to bend his knee freely without the movement of his tibia being blocked in any way by the articulation of the splint.

As a result, the splint does not impose any downward vertical axial constraint in anteroposterior compression by the displacement in beinding, but a strict holding of the movements of internal or external laterality at the knee.

As shown in the drawing, to limit the direction of rotation of the lower upright 6 to the single direction corresponding to the bending of the knee from its position of alignment with the upper upright 5, as shown in FIG. 2, the longitudinal edge of the rod 7, located on the side opposite to this direction, is provided with a wing 7a opposing any pivoting of the lower upright 6 in the opposite direction.

In the example shown in FIGS. 1-4 of the drawing, the wing 7a allows a pivoting of the lower upright 6 around its associated pin 12 and of the rod 7 around the pin 11 of the upper upright 5 in the direction of the arrow 14 (FIG. 2) but opposes their pivoting in the direction of arrow 15 (FIG. 2).

FIG. 4 shows one side portion of a splint of the present invention in which the connecting pins 11 and 12 of each portion of the splint are pivot pins fastened by screwing them into respective threaded apertures in the corresponding upright 5 or 6 and whose free end exhibits a shoulder 11a and 12a respectively, able to assure the holding and guiding of the rod 7. For this purpose, the length of each of the pivot pins 11 and 12 corresponds to the thickness of the rod 7 increased by functional play.

FIGS. 5 to 7 show two variant embodiments of a splint according to the present invention, whose purpose is to limit the rotation of the lower upright 6 of each portion, both in the bending direction and in the direction of maximal open of the patient's leg.

In the example illustrated in FIGS. 1 to 4, the maximal opening angle is determined by the wing 7a carried by the rod 7 and is set at the maximal opening possible, i.e. 180°. On the other hand, limitation of the bending angle is not provided which, in some cases and particularly during a period of reeducation of a patient, can be desirable.

To achieve this end, according to the two embodiments illustrated in FIGS. 5 to 7, not only is there provided a limitation of the rotation of the lower upright 6 between the two desired maximum angles, but in addition, the upper upright 5 is immobilized against rotation in relation to the rod 7.

In the example as shown in FIG. 5, the maximum opening angle is, as shown in FIGS. 1 to 4, 180°, i.e. in this position the two portions 5 and 6 are in alignment with one another. This result is obtained by the wing 7a of the rod 7 directly comparable to the wing 7a of the above-mentioned example.

To limit the angular clearance of the lower element 6 in the direction of the arrow 14 to a bending angle a, in the embodiment shown in FIG. 5, the edge of the rod 7 opposite that which carries the wing 7a, carries a second wing 7b exhibiting respectively two section 7'b and 7"b, corresponding to the desired maximum angle a.

In the example shown in FIG. 5, the section 7'b of the wing 7b is parallel to the wing 7a to immobilize the upper upright 5 in rotation obviously without opposing longitudinal movement of the rod 7 in relation to it. Consequently, the two movements of each portion of the splint are now separated, namely: the rotation of one upright in relation to the other is exclusively reserved for connection of the lower upright 6 on the pin 12, while the longitudinal movement of an upright in relation to the other in a direction corresponding to moving the pins 11 and 12 together or apart is reversed exclusively for the connection of the upper upright 5 on the pin 11.

In a variant embodiment of the invention shown in FIGS. 6 and 7, the means assuring immobilization in rotation of the upper upright 5 and limiting rotation of the lower upright 6 in both directions, are made up of pairs of pins 16 and 17 respectively fastened to the rod 7 perpendicular to its face against which the uprights 5 and 6 of this portion of the splint are applied.

In this example, according to a simple embodiment of the present invention, each of the pins 16 and 17 of each pair of pins is fastened to the rod 7 by screwing it into a respective threaded bore or aperture provided to receive it in the rod.

As shown not only in FIG. 6 but also in FIG. 7, according to an advantageous arrangement of this embodiment, there is provided, for each of the pins 17 limiting the angular clearance of the lower upright 6, at least a second threaded bore or aperture 17a so that it is possible, before putting the splint on the patient, to choose the maximal bending angle a1 or a2, most suited to the patient and also the maximal opening angle since if, in the example shown in FIG. 6, the maximal opening between the uprights 5 and 6 correspond to their alignment, in the example shown in FIG. 7, the maximal opening angle b is less than 180°.

This arrangement further offers the advantage of modifying the lower maximum angle a, for example, by reducing its value, i.e., by moving one of the pins 17 (that on the right in FIGS. 6 and 7) from the position shown in FIG. 7 corresponding to the greatest value a1 of the lower maximum angle to its position shown in FIG. 6 corresponding to the slightest value a2 of the lower maximum angle of angular clearance of the uprights 5 and 6.

In the same way, it is possible to move the second pins 17 (on the left in FIGS. 6 and 7) from its position shown in FIG. 7 to that shown in FIG. 6 and thus allow the patient maximal opening of his leg.

Naturally, the movements of the pins 17 can be performed during the period of re-education of the patient as a function of the development of this re-education.

As can be easily be conceived, the embodiments of FIGS. 6 and 7 exhibit, in relation to that of FIG. 5, the advantage of a choice of the maximum opening and minimum bending angles, both during putting on of the splint and during re-education of the patient, as would be the case with a splint according to that shown by FIG. 1.

Further, it can easily be appreciated that the modification of angles, by placement of the pins 17, can be made without it being necessary to remove the patient's splint, i.e., without destroying the casts which assure their fastening to his leg.

It is to be appreciated that the foregong description and accompanying figures of drawings relate to preferred embodiments given by way of example, not by way of limitations. It is to be understood that numerous other embodiments and variants are possible without departing from the spirit and scope of the present invention, its scope being defined in the appended claims.

What is claimed is:

1. An articulated splint for a knee joint of the type having two symmetrical portions which are to be respectively placed on respective sides of a leg of a patient and held in place by upper and lower parts of a cast which has its central part absent to allow movement of a knee of a patient, the splint comprising said two symmetrical portions, each of said symmetrical portions including a first, upper, femoral upright and a second, lower, tibial upright; said first upright and said second upright being intended to be fastened with respective corresponding uprights of the opposite one of said symmetrical portions by the respective upper and lower parts of the cast; a first pin defining an axis of rotation of said rod with respect to one of said uprights and extending through said rod; and a second pin defining a point of movement of said rod with respect to the other of said uprights and extending through said rod, said second pin being positioned in an elongated aperture in the other of said uprights and said elongated aperture having its longitudinal axis oriented in the direction of said first pin, wherein, to limit rotation of said second, tibial upright to a single direction from its position in alignment with said first, femoral upright, said rod of each of said portions exhibits, along its edge opposite that of the direction of rotation of said second, tibial upright, a wing forming a stop for each of said uprights.

2. An articulated splint according to claim 1, wherein said elongated aperture is in said second, tibial upright and wherein said second pin extends through said second, tibial upright and connects same to said rod.

3. An articulated splint according to claim 1, wherein each respective one of said pins connecting respective said uprights to said rod is fixed to pivot the corresponding one of said uprights and whose free end has a shoulder assuring holding and guiding of said rod, the length of pivot corresponding to the thickness of said rod increased to provide play necessary for functioning.

4. An articulated splint for a knee joint of the type having two symmetrical portions which are to be respectively placed on respective sides of a leg of a patient and held in place by upper and lower parts of a cast which has its central part absent to allow movement of a knee of a patient, the splint comprising said two symmetrical portions, each of said symmetrical portions including a first, upper, femoral upright and a second, lower, tibial upright, said first upright and said second upright being intended to be fastened with respective corresponding uprights of the opposite one of said symmetrical portions by the respective upper and lower parts of the cast; a first pin defining an axis of rotation of said rod with respect to one of said uprights and extending through said rod; and a second pin defining a point of movement of said rod with respect to the other of said uprights and extending through said rod, said second pin being positioned in an elongated aperture in the other of said uprights and said elongated aperture having its longitudinal axis oriented in the direction of said first pin, wherein said rod of each said portion to which are connected said first upright and said second upright carries means for limiting rotation of said first upright and said second upright in one direction, to their maximal opening position and, in the other direction to a desired maximum lower angle of bending.

5. An articulated splint according to claim 4, wherein said elongated aperture is in said second, tibial upright and wherein said second pin extends through said second, tibial upright and connects same to said rod.

6. An articulated splint according to claim 4 or claim 5, wherein in case maximal opening position of said first upright and said second upright correspond to their position of alignment with one another, said means limiting, in one direction, rotation of said first upright and said second upright of each said portion to this position and, in the other direction, to their desired lower maximum angular position, comprise, on the one hand, a first longitudinal wing solid with a straight edge of said rod and, on the other hand, a second wing in the shape of a right angle solid with an opposite edge of said rod, like said second wing forming an angle at a desired lower maximum value of angulation of said first upright and said second upright.

7. An articulated splint according to claim 4 or claim 5, wherein said means limiting rotation of said first upright and said second upright, in one direction, to their maximal opening position and, in the other direction, to a desired maximum angle of bending, are pin-like members fastened to said rod on the same side as said first, femoral upright and said second, tibial upright.

8. An articulated splint according to claim 7, wherein each of said pin-like members is fastened by screwing in a respective threaded bore provided to receive it in said rod.

9. An articulated splint according to claim 8, wherein said rod has at least one additional threaded bore corresponding to another value of at least one additional maximum angle.

10. An articulated splint according to claim 4 or claim 5, wherein said means limiting rotation of said first upright and said second upright in relation to one another, in one direction, to their maximal opening and, in the other, to the desired lower maximum angle of bending, are operatively arranged to immobilize one of said uprights in rotation, preferably the upper femoral upright.

11. An articulated splint according to claim 10, wherein said first pin which extends through said rod is that on which said upper, first, femoral upright is articulated.

* * * * *